United States Patent [19]

Li

[11] Patent Number: 5,444,089

[45] Date of Patent: Aug. 22, 1995

[54] NEUTRAL LIPIDS FROM ENDOSPERM OF JOB'S TEARS

[75] Inventor: Da P. Li, 3-201, 19 Youdian Road, Hangzhou, China

[73] Assignees: Da P. Li; Zhejiang Provincial Hospital of Traditional Chinese Medicine, both of Hangzhou, China

[21] Appl. No.: 120,549

[22] Filed: Sep. 14, 1993

[30] Foreign Application Priority Data

Sep. 16, 1992 [CN] China ............................ 92110677.7
Sep. 17, 1992 [CN] China ............................ 92110839.7
Jan. 1, 1993 [CN] China ............................ 93100735.6

[51] Int. Cl.$^6$ ............................................ A61K 35/78
[52] U.S. Cl. ............................. 514/547; 514/549; 514/552; 554/9; 554/12; 554/13; 554/14
[58] Field of Search ................. 514/547, 549, 552; 554/9, 12, 13, 14

[56] References Cited

FOREIGN PATENT DOCUMENTS 55-035052 9/1978 Japan .
58-210022 6/1982 Japan .
58-213719 6/1982 Japan .
61-204131 3/1985 Japan .
63-190809 2/1987 Japan .

OTHER PUBLICATIONS

Zhejiang Pharmacology, vol. 3:18–20, (1986).
Pharmacology Abstracts, p. 129, (1960).
Foreign Pharmacology, Chinese Traditional Medicine, pp. 19–20, (1989).
Kinjiang Chinese Traditional Medicine, p. 42, (1989).
Chinese Traditional Ready–Made Medicine, p. 38, (1990).
Chemical Abstract, pp. 8858–8860, (1962).
Ukita et al. "Studies on the Anti–Tumor Component in the Seeds of *Coix lachryma-jobi* L. Var. Ma-Yuen (Roman.)", UDC, vol. 9:43–46, (1961).
Si Pei–Hai, "The Extraction of the Oil Of the Endosperm of Job's Tears and the Preparatoin of its Emulsion," Zhejiang Pharmacology, vol. 3:18–20 (1986).

*Primary Examiner*—Richard L. Raymond
*Attorney, Agent, or Firm*—Foley & Lardner

[57] ABSTRACT

The present invention provides anti-tumor neutral lipids of the endosperm of Job's tears (Coix lachrymajobi), a method to extract and refine it from the endosperm of Job's tears and a pharmaceutical composition containing the neutral lipids. The neutral lipids of the endosperm of Job's Tears and its pharmaceutical composition are indicated for anti-tumor effect, enhancement of immunity and protection from many diseases.

15 Claims, 5 Drawing Sheets

NEUTRAL LIPIDS FROM ENDOSPERM OF JOB'S TEARS

BACKGROUND OF THE INVENTION

1. Field

The present invention concerns neutral lipids with anti-tumor effect its extraction and refinement and pharmaceutical composition. More specifically, the invention concerns neutral lipids from the endosperm of Job's tears, a method to extract and refine the lipids from the endosperm and an anti-tumor emulsion of the neutral lipids from the endosperm of Job's tears for injection and oral administration.

The endosperm of Job's tears is a dry endosperm of Coix lachryma-jobi. It has been used as a traditional medicine and nourishment for thousands of years in China.

In 1961, Tyunosin Ukita and Akio Tanimura (Ukita T. et. al., Chem. Pharm. Dull, 9(1):43, 1961) reported an extraction for coixenolide from the endosperm of Job's tears as an anti-tumor element and the results of its anti-tumor activity tests. They reported also the formula of coixenolide as $C_{38}H_{70}O_4$, however, the pharmaceutical preparation thereof was not mentioned. It was reported to inhibit the growth of mouse Ehrlich ascites tumor.

Coixenolide was extracted by the following steps:

Powder of the endosperm was extracted with acetone 3 times. The extract was dissolved in petrol ether, filtered and concentrated to a brown syrup which was dissolved in petrol ether, run through a silica gel column with petrol ether and 0.2N KOH was added to separate the acidic components. The neutral oil was run through an alumina column and a silica column. Coixenolide was obtained as a pure compound and exhibited strong anti-tumor activity. But there is no report about its clinical application. Because of the two kinds of column chromatography (alumina and silica) used in the extraction and refinement, the yield of coixenolide was quite low. Thus it was very expensive to obtain, and no commercial products have resulted.

In the eighties, Si Pei-hai obtained a crude oil from endosperm of Job's tears directly with petrol ether and made it up as an intravenous emulsion (Si Pei-hai, The Extraction of the Oil of the Endosperm of Job's Tears and the Preparation of its Emulsion, Zhejiang Pharmacology, 3(6):18–20, 1986). The extraction and refinement steps of the oil of the endosperm of Job's tears was as follows:

Powder of the endosperm of Job's tears was extracted with petroleum ether (3 times). The extract was purified by absorption, decoloration and evaporation to obtain the oil of the endosperm of Job's tears. The oil had a relative density of 0.9033–0.9057 (20° C.) a diopter value of 1.4670–1.4708 (20° C.), an iodine value of 83–90 and an acid value of <36.

The intravenous emulsion comprised the oil extracted with above method (as the main component), and two emulsifiers, spans and tween. The composition was:

| Oil from the endosperm of Job's tears | 10 g |
|---|---|
| Spans-80 | 1 g |
| Tween-80 | 1.5 g |
| Water for injection use | q.s. to 100 ml |

The intratumor emulsion was just used for the research of pharmaceutical preparation and its body distribution. There are the following obstacles for the intraemulsion to be used for human clinical use:

1. The main component, the oil from the endosperm of Job's tears, was not pure and safe enough to meet the requirement of Chinese Pharmacopoeia, e.g., its acid value must be controlled just below 36.

2. Tween and spans can get through cell membrane, and are lyso-active and toxic. A suitable isoosmoticum must be used to prevent lysogenesis. Actually, most commercial intravenous emulsion products of England, Germany, the United States, France, China and Japan do not use emulsifiers like tween and spans.

3. The above composition does not include the essential element of isoosmoticum, thus is not reasonable.

SUMMARY OF THE INVENTION

The aim of the present invention is to provide an extraction and refinement process to obtain anti-tumor neutral lipids from the endosperm of Job's tears (NLEJ). The method as indicated has simple steps, is inexpensive, but yields a standard neutral lipids composition meeting the need of intravenous use.

Another aim of the present invention is to provide a pharmaceutical composition with NLEJ, and to prepare an O/W emulsion as an anti-tumor drug. The composition is safe and reasonable enough to be used for oral, intravenous or intraartery administration.

DETAILED DESCRIPTION

NLEJ of the present invention is a light yellow transparent liquid at room temperature. NLEJ is easily dissolved in petrol ether, ether and benzene, soluble in acetone, slightly soluble in methanol and alcohol, and insoluble in water. Tested as an oil, NLEJ has physicochemical constants as follows: acid value <0.20, iodine value 95.00–107.00, saponification value 185.00–195.00, relative density 0.915–0.918(20° C.), diopter value 1.470–1.475(20° C.). NLEJ comprise triglyceride (91.48±3.43%), diglyceride(1.47±0.63%), monoglyceride(5.75±3.19%) and alkylacylacetin(1.0±0.78%). The lipoclastic fatty acid resides comprise hexadecanoic, octadecanoic, octadecenoic and octadecadienoic acid.

The extraction and refinement of NLEJ is as follows: Extraction by organic solvent: the organic solvent is, e.g., acetone, petrol ether, ether, alcohol or hexane. The extraction method is e.g., percolation, filtering or seeping through the powder of endosperm of Job's tears. Crude oil will be extracted with big amounts of foreign matter, e.g. free fatty acids, and pigments.

Absorption and decoloration: A common absorbent is used, i.e., 1% active carbon, 3% white potter's clay, 10% alumina, or others. Yellow oil will be obtained after the crude extract is absorbed;

Alkalizing saponification: after a suitable amount of alkaline solution (e.g. NaOH or KOH) is added for saponification, an emulsion will result; Deemulsification by acetone: a suitable amount of acetone will cause the emulsion to be transparent;

Liquid-liquid extraction: a suitable amount of a second organic solvent, e.g., petrol ether, ether or hexane is used. The liquid is extracted and allowed to settle, the phase containing mainly acetone (containing acidic element, water) is discarded, and the organic solvent is evaporated, leaving a residue comprising mainly NLEJ of the present invention.

Refinement: between the steps of alkalization saponification and deemulsification with acetone, a step of washing the emulsion with hot water may be added, and/or after the liquid-liquid extraction step, one step of decoloration and/or washing by hot water may be added if necessary. Then NLEJ of high purity meeting the need of intravenous use is obtained.

The emulsion of the present invention, as a pharmaceutical composition, contains NLEJ as the main component, soy (or egg) lecithin as an emulsifier and enough water. It also contains glycerol, sorbitol or the like as an isoosmoticum. It may also contain other conventional anti-tumor drugs. The method of emulsification includes two conventional steps, homogenization and dispersion. Within the pharmaceutical composition the content of NLEJ could vary in a wide range. It is an O/W type emulsion. Within 100 ml of the emulsion, NLEJ ranges from 5-25 g.

Utility, Testing and Administration

General Utility

NLEJ and its pharmaceutical composition of the present invention has a high anti-tumor activity. The latter can be especially used in the therapeutics of lung cancer, hepatic carcinoma and other metastasizing cancers of middle or late state. It can enhance body immunity and protect the body from many diseases. It can also be used in treating immune deficiency diseases. The combination of NLEJ emulsion with small doses of chemotherapy can strengthen the anti-tumor activity and reduce the toxicity of chemotherapy.

Testing

Testing of the anti-tumor activity of NLEJ and its pharmaceutical composition on human tumor will now be illustrated by Example 9 and Example 10. The effects of this pharmaceutical composition on immunity, the enhancement of the combination with small doses of chemotherapy and the protective effect on the decrease of leukocyte induced by chemotherapy will be illustrated, respectively, in Example 11, Example 12 and Example 13, and the clinical effects of this pharmaceutical composition are described in Example 14.

Administration

The compounds of this invention were administered at a therapeutically effective dosage, i.e. the amount which, when administered to a mammal in need thereof, is therapeutically sufficient for effective treatment of tumor diseases. Administration of the active compounds herein could be intravenous, intraartery or oral.

EXAMPLES

The following examples are given to enable those skilled in the art to more clearly understand and to practice the present invention. They should not be considered as limiting the scope of the invention, but merely as being illustrative and representative thereof.

Example 1

Extraction and Refinement of NLEJ 100 kg powder of the endosperm of Job's tears was extracted with acetone, and 5 kg of extract was obtained after the evaporation of acetone, absorbed and decolored. 152 g NaOH (or relative amount of KOH) was dissolved to form a 5% hot alkaline solution, which was added for alkalizing saponification. The weight of alkaline added depended on the acid value of the extract. The high temperature of alkaline made the saponification more rapid and thorough. The emulsion was separated after it settled, and washed 2-3 times until the emulsion turned neutral (pH 6-7). 1:1 (v/v) acetone was added for deemulsification, and, after settlement, the acetone phase was extracted with enough petrol ether, was allowed to settle and the acetone was discarded. NLEJ remained in the petrol ether. An absorbent was added for pigments and pyrogen, and neutral oil was obtained after filtration and petrol ether evaporation, then boiled for 0.5 hr with hot distilled water under vacuum, and was allowed to settle. The neutral oil was heated to 100° C. to evaporate water, the absorbent was added again and filtered out, and 2 kg light yellow NLEJ of the present invention was obtained, and packaged for preparing intravenous and oral emulsions, after heating to 160° C. for 2 hr for sterilization.

The absorbent mentioned above is active carbon, white pottery clay, alumina or others.

Examples 2-8

Compositions of NLEJ emulsion

The compositions for oral use, intravenous and intraartery use will be illustrated in detail in Examples 2-8.

Example 2

| NLEJ | 10.0 g |
| --- | --- |
| Soy lecithin for injection use | 1.5 g |
| Glycerol for injection use | 2.5 g |
| Water for injection use | q.s. to 100 ml |

The emulsion was an oral, intravenous or intraartery emulsion.

Example 3

| NLEJ | 10.0 g |
| --- | --- |
| Lecithin for injection use | 1.2 g |
| Glycerol for injection use | 2.5 g |
| Water for injection use | q.s. to 100 ml |

The emulsion was an intravenous or intraartery emulsion.

Example 4

| NLEJ | 15.0 g |
| --- | --- |
| Pluronic F88 | 2.0 g |
| Glycerol | 2.5 g |
| Distilled Water | q.s. to 100 ml |

The emulsion was an oral emulsion.

Example 5

| NLEJ | 15.0 g |
|---|---|
| Soy lecithin for injection use | 2.0 g |
| Glycerol for injection use | 2.5 g |
| Water for injection use | q.s. to 100 ml |

The emulsion was an intravenous or intraartery emulsion.

Example 6

| NLEJ | 5.0 g |
|---|---|
| Phospholipid | 0.75 g |
| Glycerol | 1.25 g |
| Distilled Water | q.s. to 100 ml |

The emulsion was an oral emulsion.

Example 7

| NLEJ | 2.5 g |
|---|---|
| Phospholipid | 2.5 g |
| Glycerol | 3.0 g |
| Distilled Water | q.s. to 100 ml |

The emulsion was an oral emulsion.

Example 8

| NLEJ | 1000 g |
|---|---|
| Soy lecithin for injection use | 120 g |
| Glycerol for injection use | 250 g |
| Water for injection use | q.s. to 100 ml |

The emulsion was an intravenous or intraartery emulsion.

Example 9

Anti-tumor Activity of NLEJ in vitro (1) Effect of NLEJ on Inhibition of Proliferation Leukemia P388 and L1210 Cultured Cells Methods 20 μl NLEJ was added in different concentrations into the 96 wells microplate of cultured leukemia cell lines in duplicate, 20 μl phosphate-buffered saline (PBS) was added into the control wells, $9 \times 10^5$ cells were in each well, the highest concentration of NLEJ was 100 μl/ml. Cells were incubated for 48 hr at 37° C. and under 5% $CO_2$, cells were counted with a Coulter Counter, and the inhibition ratio and the concentration of drug which inhibited 50% of the colony proliferation of the tumor cells ($IC_{50}$) was calculated:

Inhibition ratio=((cell number of control- cell number of treatment)/(cell number of control- cell number at the beginning of test))×100%

Results

Figure 1:
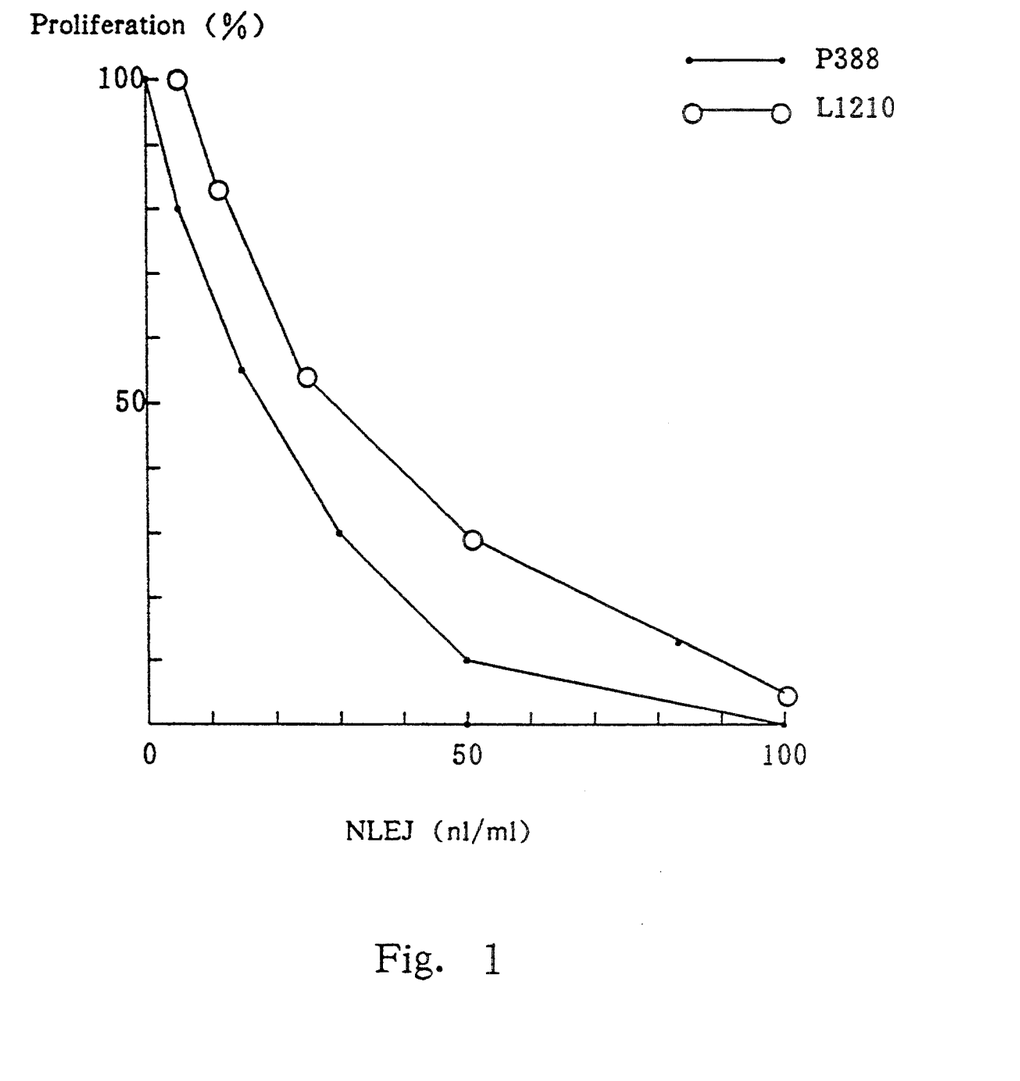
FIG. 1 Effect of NLEJ on Proliferation of Leukemia P388, L1210

NLEJ showed evident anti-tumor activity in leukemia P388 and L1210-cells in vitro. The dosage above 50 μl/ml inhibited almost all cell proliferation. The $IC_{50}$ of NLEJ on P388 and L1210 cells were 15.2 μl/ml and 28.8 μl/ml respectively. Their coefficients of correlation were 0.9136 and 0.9454 respectively (FIG. 1 and Table 1).

TABLE 1

Effect of NLEJ on Proliferation Leukemia P388, L1210 and Colon Tumor M7609 Cells $IC_{50}$ of NLEJ

| P388 | L1210 | M7609 |
|---|---|---|
| 15.1 | 28.8 | 11.9 |

(2) Test on Formation Inhibition of Colon Tumor M7609 Cell Colony 0.1 ml suspension of colon tumor (M7609) cells (2000 /ml) at logarithmic stage were prepared after digestion with 0.15% trypsin, and added to 3.8 RPMI 1640 medium containing 20% bovine serum in d-4 cm round cell container for incubation. 0.1 ml NLEJ of different concentrations were added to the container after 24 hr incubation at 37° C. and under 5% $CO_2$. The cells were incubated for 9 days more, and after dyeing with 0.1% crystal violet in alcohol the colony was counted, and the colony formation inhibition ratio and $IC_{50}$ were calculated.

Results

Figure 2:
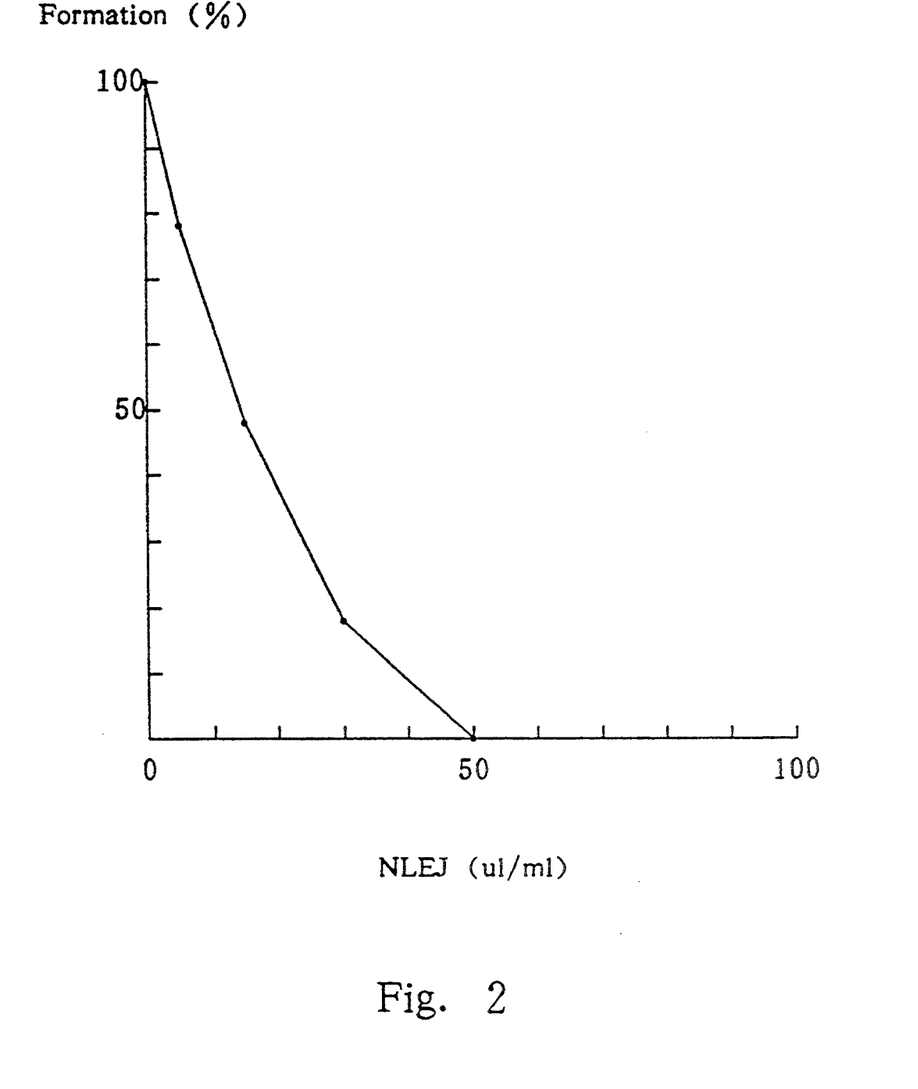
FIG. 2 Effect of NLEJ on Formation of Cell Colony of Colon Tumour M 7609

NLEJ markedly inhibited the formation of cell colonies of colon tumor M7609. The concentration of 50 μl/ml inhibited all formation. The $IC_{50}$ of NLEJ on the formation of cell colony of colon tumor M7609 was 11.88 μl/ml. Their coefficient of correlation was 0.94445 (FIG. 2 and Table 1).

Example 10

Therapeutic Effect of NLEJ Emulsion on Metastasizing Tumor in vivo (1) Therapeutic Effect of NLEJ Emulsion on Growth of Human Hepatoma (QGY) in vivo Methods Hepatoma (QGY) tissues growing luxuriantly were homogenized in physical saline (1:4) and prepared as a suspension. Each nude mouse was inoculated subcutaneously with 0.2 ml of the suspension at its armpit. The nude mice were divided into groups at random the next day. The doses of NLEJ emulsion were 25 ml/kg, 12.5 ml/kg and 6.25 ml/kg. The emulsion was administrated intravenously at the tail of the nude mouse every day for 10 days. One group of mice were administered with cyclophosphamide (CTX) of a dose of 30 mg/kg intraperitoneally every day for 7 days. The nude mice of the control group were administered with a similar emulsion just absent the NLEJ (blank emulsion) at a dose of 25 ml/kg intravenously at the tail of the nude mouse every day for 10 days. Tumor tissues of all nude mice were sampled and weighed 30 days after inoculating.

Results

All doses of NLEJ emulsion, 25 ml/kg, 12.5 ml/kg and 6.25 ml/kg, showed good therapeutic effect on the growth of human hepatoms (QGY), and good dose-activity correlation relationship. The highest dose (25 ml/kg) had an inhibition ratio almost as high as the treatment of CTX (Table 2).

TABLE 2

Therapeutic Effect of NLEJ Emulsion on Growth of Human Hepatoma (QGY) in vivo

| Sample | Dose | Number | Tumor (g) | Inhibition % | P Value |
|---|---|---|---|---|---|
| NLEJ | 6.25 ml/kg | 5/5 | 1.68 ± 0.52 | 49.70 | <0.01 |
| NLEJ | 12.5 ml/kg | 5/5 | 1.02 ± 0.31 | 61.08 | <0.01 |
| NLEJ | 25.0 ml/kg | 5/5 | 0.54 ± 0.21 | 83.83 | <0.01 |
| CTX | 30 mg/kg | 5/5 | 0.28 ± 0.08 | 91.00 | <0.01 |
| Control | 25 ml/kg | 515 | 3.34 ± 0.86 | — | — |

(2) Therapeutic Effect of NLEJ Emulsion on Growth of Human Small Cell Lung Cancer (SPC) in vivo Methods SPC tumor tissues growing luxuriantly were cut into pieces of 2 mm, one of the pieces was inoculated under the skin of the armpit of each nude mouse. Nude mice were divided into groups at random the next day and one group was administered with the NLEJ emulsion at a dose of 25 ml/kg iv×10 (qd), one group of mice was administered with dacarbazine (DTIC) at a dose of 40 mg/kg iv×10 (qd), and the nude mice of the control group were administered with blank emulsion at a dose of 25 ml/kg iv×10 (qd). Tumor tissues of all nude mice were sampled and weighed 30 days after inoculating.

Results

The dose of 25 ml/kg of NLEJ showed good therapeutic effect on human small cell lung cancer. The inhibition ratio was as high as 62.35% (Table 3).

TABLE 3

Therapeutic Effect of NLEJ Emulsion on Growth of Human Small Cell Lung Cancer (SPC) in vivo

| Sample | Dose | Number | Tumor | Inhibition % | P Value |
|---|---|---|---|---|---|
| NLEJ | 25 ml/kg | 5/5 | 1.34 ± 0.32 | 62.35 | <0.01 |
| DTIC | 40 mg/kg | 5/5 | 0.18 ± 0.04 | 94.94 | <0.01 |
| Control | 25 ml/kg | 5/5 | 3.56 ± 0.83 | — | — |

(3) Therapeutic Effect of NLEJ Emulsion on Metastasis of Melanoma (B16) in Lung in vivo Methods Melanoma B16 tissues growing at logarithmic stage were digested with 0.15% trypsin, and 0.2 ml suspension of $2.5 \times 10^5$ cells/ml in RPMI 1640 medium from the tissues was inoculated intravenously into the tail of each C57BL/6 mouse. Mice were divided into groups at random 3 days after inoculating and were administered different emulsions. Mice were killed 21 days after inoculating, and metastasized colonies of melanoma in mouse's lung were counted to calculate the inhibition ratio and compare the different effects of different administrations of NLEJ emulsion on metastasis of malanoma in lung. 100 mg/kg cyclophosphamide (CTX) was administered in the same way to compare with NLEJ emulsion.

Results

The different effect of different administrations on metastasis of melanoma.

Figure 3:
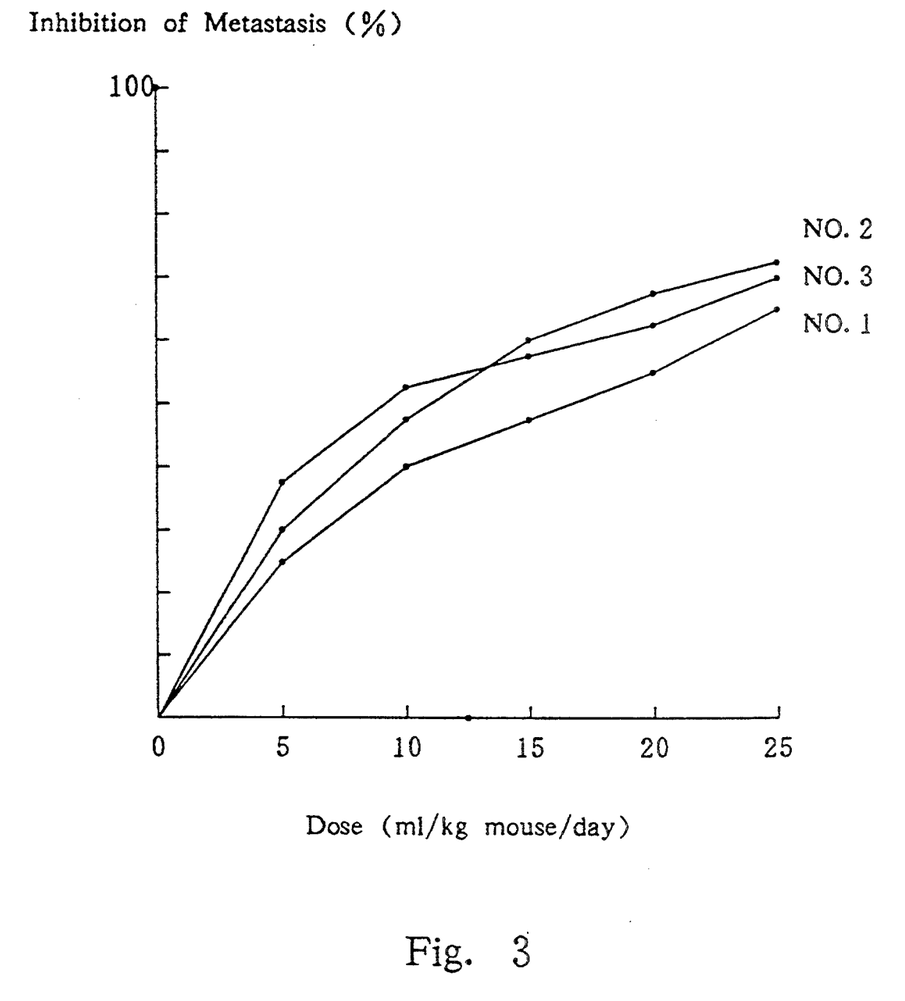
FIG. 3 Therapeutic Effect of NLEJ Emulsion on Metastasis of Melanoma (B16) in Lung in vivo (every third day)

(i) All combinations of dose (6.25 ml/kg, 12.5 ml/kg and 25 ml/kg) and administration (every third day, 4 times and intravenously at tail) of NLEJ emulsion showed evident inhibition effect on metastasis of melanoma B16 (Table 4, FIG. 3).

TABLE 4

Therapeutic Effect of NLEJ Emulsion on Metastasis of Melanoma (B16) in Lung in vivo (every third day)

| Sample | Dose (ml/kg) | Admin. | No. | Colony No. (X + SD) | Inhibition (%) | P value |
|---|---|---|---|---|---|---|
| NLEJ | 6.25 | iv × 4 (3, 5, 7, 9) | 30/30 | 93.43 ± 15.74 | 36.88 | <0.01 |
| NLEJ | 12.5 | iv × 4 (3, 5, 7, 9) | 30/30 | 79.87 ± 19.02 | 46.08 | <0.01 |
| NLEJ | 25.0 | iv × 4 (3, 5, 7, 9) | 30/30 | 47.83 ± 15.53 | 67.76 | <0.01 |
| CTX | 100 mg/kg | ip × 2 (3, 5) | 30/30 | 18.80 ± 8.50 | 95.90 | <0.01 |
| CK | 25.0 | iv × 4 (3, 5, 7, 9) | 30/30 | >147 | — | — |

Figure 4:
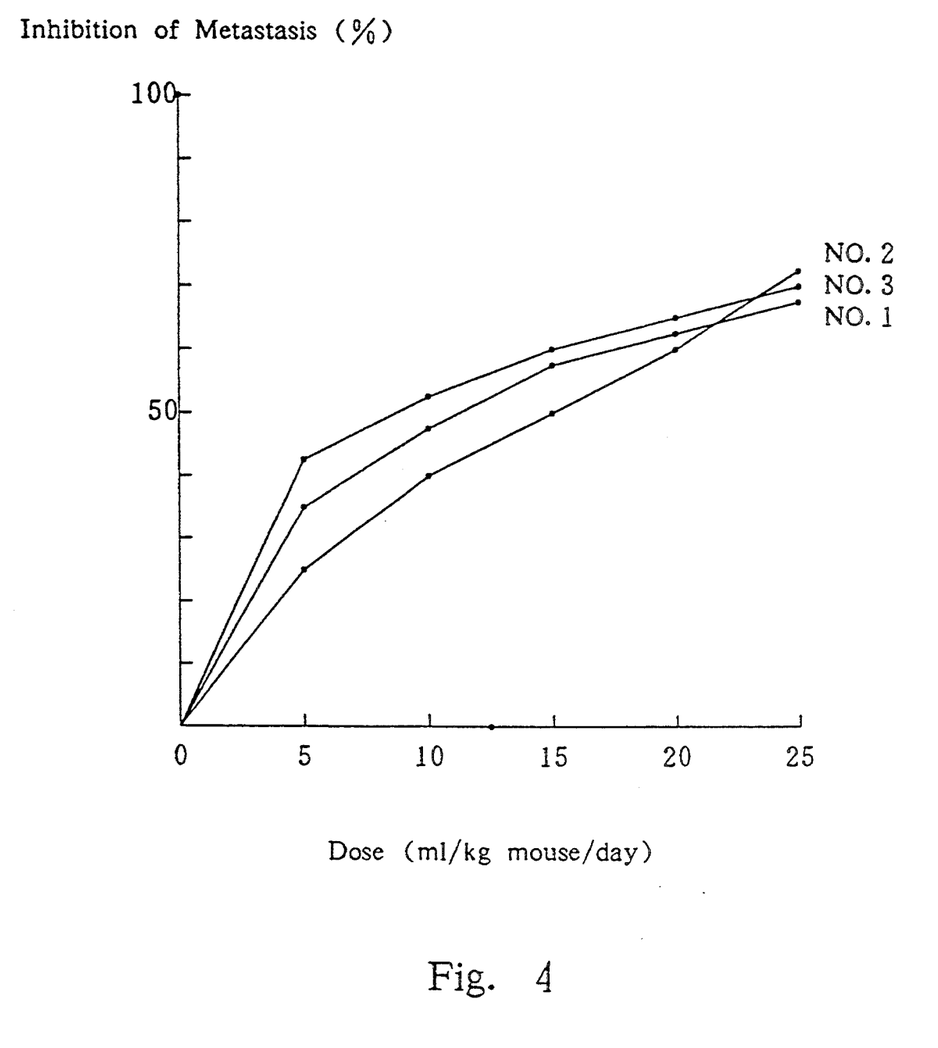
FIG. 4 Therapeutic Effect of NLEJ Emulsion on Metastasis of Melanoma (B16) in Lung in vivo (iv, every day)

(ii) All combinations of dose (6.25 ml/kg, 12.5 ml/kg and 25/kg) and administration (every day, 7 times and intravenously at tail) of NLEJ emulsion showed evident inhibition effect on metastasis of melanoma B16 (Table 5, FIG. 4).

TABLE 5

Therapeutic Effect of NLEJ Emulsion on Metastasis of Melanoma (B16) in Lung in vivo (iv, every day)

| Sample | Dose (ml/kg) | Admin. | No. | Colony No. (X + SD) | Inhibition (%) | P value |
|---|---|---|---|---|---|---|
| NLEJ | 6.25 | iv × 7 | 30/30 | 83.23 ± 22.82 | 44.87 | <0.01 |
| NLEJ | 12.5 | iv × 7 | 30/30 | 51.87 ± 13.28 | 63.31 | <0.01 |
| NLEJ | 25.0 | iv × 7 | 30/30 | 32.83 ± 11.80 | 78.77 | <0.01 |
| CTX | 100 mg/kg | ip × 2 (3, 5) | 30/30 | 8.0 ± 6.22 | 98.67 | <0.01 |
| CK | 25.0 | iv × 7 | 30/30 | >155 | — | — |

Figure 5:
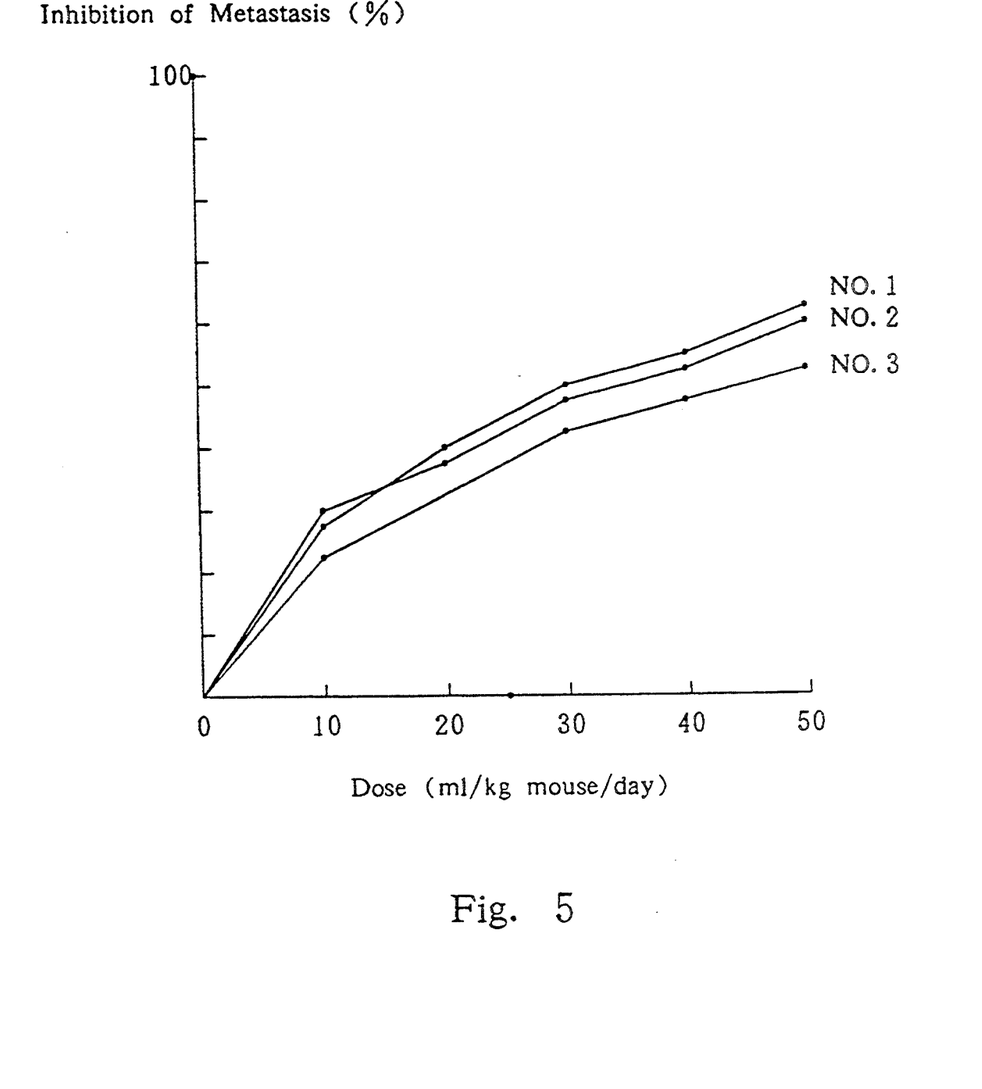
FIG. 5 Therapeutic Effect of NLEJ Emulsion on Metastasis of Melanoma (B16) in Lung in vivo (ip, every day)

(iii) All combinations of dose (6.25 ml/kg, 12.5/kg and 25/kg) and administration (every day, 7 times, and intraperitoneal) of NLEJ emulsion showed evident inhibition effect on metastasis of melanoma B16 (Table 6, FIG. 5).

TABLE 6

Therapeutic Effect of NLEJ Emulsion on Melanoma (B16) in Lung in vivo (ip, every day)

| Sample | Dose (ml/kg) | Admin. | No. | Colony No. (X + SD) | Inhibition (%) | P value |
|---|---|---|---|---|---|---|
| NLEJ | 6.25 | iv × 7 | 30/30 | 80.47 ± 18.18 | 29.25 | <0.01 |
| NLEJ | 12.5 | ip × 7 | 30/30 | 68.50 ± 16.77 | 39.64 | <0.01 |
| NLEJ | 25.0 | ip × 7 | 30/30 | 47.07 ± 13.72 | 58.28 | <0.01 |
| CTX | 100 mg/kg | ip × 2 (3, 5) | 30/30 | 0 | 100 | <0.01 |
| CK | 25.0 | ip × 7 | 30/30 | >114 | — | — |

Example 11

Enhancement of Mouse Immunity from NLEJ Emulsion (1) Inducement of Proliferation of Mouse Spleen Lymphatic Cell from NLEJ Emulsion in vitro Methods Spleen cells were obtained aseptically from C57BL/6 mouse. The cell density was regulated to be $1 \times 10^7$/ml with RPMI-1640 medium. Each cell hole contained 100 μl medium, 100 μl drugs and 50 μl ConA. The drugs were NLEJ emulsion (4 concentrations), lentinanin (4 concentrations), blank emulsion and water. 4 duplications were prepared for each treatment. Cells were incubated for 48 hr at 37° C. and under 5% $CO_2$, then $^3$H-Tdr was added to the wells (0.5 μci/well), and incubated 20 hr more. Cells were collected and CPM values were measured with a liquid scintillation counter.

Results

It can be seen in Table 7 that the cells incubated with both NLEJ and lentinanin got a higher CPM value, i.e., both NLEJ and lentinanin induced the proliferation of mouse spleen lymphatic cells in vitro. The correlation relationship between dose and CPM value also is shown.

TABLE 7
Inducement of Proliferation of Mouse Spleen Lymphatic Cell from NLEJ Emulsion and Lentinanin in vitro

| Treatment | Sample (Concentration) | CPM (X + SD) |
|---|---|---|
| NLEJ | 100 (1:4) | 7765 ± 1008** |
| NLEJ | 100 (1:2) | 7165 ± 1163** |
| NLEJ | 100 (1:1) | 6540 ± 946** |
| NLEJ | 100 (mother) | 6230 ± 1130** |
| Leutinanin | 100 (1:4) | 11555 ± 1279** |
| Leutinanin | 100( 1:2) | 11025 ± 1133** |
| Leutinanin | 100 (1:1) | 7700 ± 747** |
| Leutinanin | 100 (mother) | 7420 ± 957** |
| Blank | 100 (mother) | 4612 ± 719 |
| Control | 100 (mother) | 4795 ± 487 |

(2) Influence of NLEJ Emulsion on the Activity of Natural Killer Cell of Mouse in vitro Methods Spleen cells were obtained aseptically from C57BL/6 mouse as effective cells, cell density was regulated to be $1 \times 10^6$/ml, the density of aim cells, YAC-1 cells, were regulated to be $1 \times 10^4$. The two suspensions of cells were mixed in 1:1 (v/v), i.e., the ratio between effective and aim cells was 1:100. $^3$H-Tdr was added to the wells (0.5 μci/well), and cells were incubated for 48 hr at 37° C. and under 5% $CO_2$. Cells were collected and CPM values were measured with a liquid scintillation counter. Specific inhibition ratio (Pi) was indicated as the activity of natural killer cell. The Pi of NLEJ emulsion was compared with the Pi of lentinanin; the blank emulsion and the medium were taken as controls.

$Pi = (1-(\text{CPM value of treatment/CPM value of control}))\times 100\%$

Results

The results showed that NLEJ stimulated the activity of natural killer cells of mouse in vitro as well as lentinanin did (Table 8). The negative correlation relationship between dose and CPM value also can be seen.

TABLE 8
Influence of NLEJ Emulsion on the Activity of Natural Killer Cell of Mouse in vitro

| Treatment | Sample (Concentration) | CPM (X + SD) | Pi % |
|---|---|---|---|
| NLEJ | 100 (1:4) | 5840 ± 1045** | 52.2 |
| NLEJ | 100 (1:2) | 6930 ± 1085** | 44.1 |
| NLEJ | 100 (1:1) | 8355 ± 1250** | 31.7 |
| NLEJ | 100 (mother) | 10925 ± 790 | 12.7 |
| Leutinanin | 100 (1:4) | 5544 ± 855** | 54.5 |
| Leutinanin | 100 (1:2) | 9395 ± 995** | 35.5 |
| Leutinanin | 100 (1:1) | 8130 ± 930** | 33.5 |
| Leutinanin | 100 (mother) | 8625 ± 1135 | 29.5 |
| Blank | 100 (mother) | 12710 ± 1125 | |
| Control | 100 (mother) | 12235 ± 725 | |

**P < 0.01 compared with Blank and Control (3) Effect of NLEJ Emulsion on Proliferation of Spleen Lymphatic Cell of Mouse Bearing Tumor in vivo Methods $1 \times 10^4$ leukemia cells L1210 were inoculated subcutaneously at each mouse's armpit. The mice were divided into 6 groups (10 mice/group) at random the next day. The 6 treatments were 6.25, 12.5, 25 ml/kg of NLEJ, 10 ml/kg of lentinanin, blank emulsion and physiological saline. The mice were killed after they were administered 7 times every day. Spleen cell suspensions were obtained aseptically from the mice regulated to have a cell density of $1 \times 10^7$/ml. 100 μl cell suspension and 100 μl medium was added into each well, duplicated for 3 wells. After being incubated at 37° C. and under 5% $CO_2$ for 48 hr, 0.5 μci/well $^3$H-Tdr was added, the cells were incubated 20 hr more, and the CPM value of collected cells was measured to compare with the control cells.

Results

It can be seen from Table 9 that NLEJ emulsion could increase the proliferation of spleen lymphatic cell of the mouse bearing leukemia. The enhancement of NLEJ emulsion on mouse immunity was also increased as the dose increased. The enhancement on mouse immunity was observed in the treatment of lentinanin.

TABLE 9
Effect of NLEJ Emulsion on Proliferation of Spleen Lymphatic Cell of Mouse Bearing Tumor in vivo

| Treatment | Dose and Administration | CPM (X + SD) |
|---|---|---|
| Lentinanin | 10 ml/kg iv × 7 | 7410 ± 770** |
| NLEJ | 6.25 ml/kg iv × 7 | 8970 ± 415** |
| NLEJ | 12.5 ml/kg iv × 7 | 10720 ± 565** |
| NLEJ | 25.0 ml/kg iv × 7 | 14330 ± 360** |
| Blank | 10 ml/kg iv × 7 | 5690 ± 1180▲ |
| Control | 10 ml/kg iv × 7 | 5230 ± 455 |

**P < 0.01 compared with blank or control
▲P < 0.01 compared with control (4) Effect of NLEJ Emulsion on Activity of NK Cell of Mouse Bearing Leukemia in vivo Methods $1 \times 10^4$ leukemia cells L1210 were inoculated subcutaneously at each mouse's armpit. The mice were divided into 6 groups (10 mice/group) at random the next day. The 6 treatments were 6.25, 12.5, 25 ml/kg of NLEJ, 10 ml/kg of lentinanin, blank emulsion and physiological saline. The mice were killed after being administered 7 times every day. Spleen cell suspensions were obtained aseptically from the mice regulated to have a cell density of $1 \times 10^6$/ml. 100 μl of the cell suspension (effective cell), 100 μl YAC cells (target cell, with the cell density of $1 \times 10^4$) and 0.5 μci/well 3H-Tdr was added into each well, duplicated for 3 wells. The cells were incubated at 37° C. and under 5% $CO_2$ for 24 hr. The CPM values of collected cells were measured. Specific inhibition ratio (Pi) was indicated as the activity of natural killer cell.

$Pi = (1-(\text{CPM value of tested group/CPM value of control group}))\times 100\%$ Results Table 10 shows the stimulation by NLEJ emulsion and lentinanin of the activity of natural killer cells of mice bearing leukemia cells, indicating the promotion of mouse immunity.

TABLE 10
Effect of NLEJ Emulsion on Activity of NK Cell of Mouse Bearing Leukemia in vivo

| Treatment | Dose and Administration | CPM (X + SD) | Pi % |
|---|---|---|---|
| Lentinanin | 10 ml/kg iv × 7 | 5660 ± 260** | 54.5** |
| NLEJ | 6.25 ml/kg iv × 7 | 10350 ± 1600 | 16.8 |
| NLEJ | 12.5 ml/kg iv × 7 | 8000 ± 960** | 34.2** |
| NLEJ | 25.0 ml/kg iv × 7 | 6210 ± 890** | 50.1** |
| Blank | 10 ml/kg iv × 7 | 12510 ± 430▲ | |
| Control | 10 ml/kg iv × 7 | 12450 ± 340 | |

**P < 0.01 compared with blank or control
▲P < 0.01 compared with control (5) Influence of NLEJ Emulsion on Induction of Interleukin-2 of Mouse Bearing Leukemia in vivo Methods $1 \times 10^4$ L1210 leukemia cells were inoculated subcutaneously at each mouse's armpit. Mice were divided into 6 groups (10 mice/group) at random the next day. The 6 treatments were 6.25, 12.5, 25 ml/kg of NLEJ, 10 ml/kg of lentinanin, blank emulsion and physiological saline. The mice were killed after they were administered 7 times every day. Spleen cell suspensions obtained aseptically from the mice were regulated to have a cell density of $1\times 10^7$/ml. 2 ml of the cell suspension containing ConA at 5 μg/ml, duplicating 3 wells. After incubation at 37° C. and under 5% $CO_2$ for 24 hr, the supernatant was used to measure the activity of interleukin-2(IL-2) with the Interleukin-2 dependent cell clone CTLL and the method of 3H-Tdr incorporation.

Results

Table 11 shows that all treatment of NLEJ stimulated the induction of interleukin-2 of the mouse bearing tumor.

TABLE 11

Influence of NLEJ Emulsion on Induction of Interleukin-2 of Mouse Bearing Leukemia in vivo

| Treatment | Dose and Administration | CPM (X + SD) |
|---|---|---|
| Lentinanin | 10 ml/kg iv × 7 | 7410 ± 770** |
| NLEJ | 6.25 ml/kg iv × 7 | 1460 ± 184 |
| NLEJ | 12.5 ml/kg iv × 7 | 2080 ± 386 |
| NLEJ | 25.0 ml/kg iv × 7 | 6020 ± 910** |
| Blank | 10 ml/kg iv × 7 | 1750 ± 487▲ |
| Control | 10 ml/kg iv × 7 | 1830 ± 95 |

**P < 0.01 compared with blank or control
▲P < 0.01 compared with control (6) Influence of NLEJ Emulsion on Phagocytosis Activity of Mouse Phagocyte in vivo Methods Swiss mice were divided into two groups at random: one group was administered NLEJ emulsion intraperitoneally 7 times every day, the other was administered blank emulsion in the same way. 0.5 ml hydrolyzed lactalbumin was administered intraperitoneally after the last administration, and 1 ml erythrocyte suspension (2%) of chicken was given the next day in the same way. 30 min later the Swiss mice were killed by the dislocation of cervical vertebra. The Swiss mice were fixed face up, the peritoneum was opened and the abdominal cavity washed with 2 ml physiological saline for 1 min. 1 ml of the water was taken out and dripped on the surface of glass. This was incubated at 37° C. for 30 min, keeping moisture. The unstuck cells were washed down, and the cells were fixed on glass with acetone:methanol 1:1(v/v). After drying, the cells were dyed with 4% Giemsa-phosphate buffer for 3 min, washed with distilled water and dried. The phagocyte (more than 100) was counted under microscope, and the phagocytosis percentage (PP) and phagocytosis index (PI) were calculated as follows:

Phagocytosis percentage = (number of phagocyte phagocytosising erythrocyte/number of the all phagocyte) × 100%

Phagocytosis index = (number of erythrocytes being phagocytosised/number of phagocyte) × 100%

Results

It can be seen in Table 12 that NLEJ promoted the phagocytosis activity of the mouse phagocyte.

TABLE 12

Influence of NLEJ Emulsion on Phagocytosis Activity of Mouse Phagocyte in vivo

| Dose/day | PP % | P value | PI % | P value |
|---|---|---|---|---|
| 6.25 ml/kg | 31.05 ± 1.96 | <0.01 | 0.68 ± 0.025 | <0.01 |
| 12.5 ml/kg | 51.45 ± 3.28 | <0.01 | 1.75 ± 0.14 | <0.01 |
| Control | 14.00 ± 1.08 | — | 0.34 ± 0.024 | — |

Example 12

Anti-tumor Activity of NLEJ Emulsion Combined with Small Dose Chemotherapy (1) Anti-tumor Therapeutical Effect on Walaer Carcinosarcoma (Solid) W256 in vivo Methods Ascites Walaer carcinosarcoma (solid) W256 tissues growing luxuriantly were digested to be a cell suspension. The cell suspension was regulated to have a $1-2\times 10^7$/ml cell density. 0.2 ml of the suspension was inoculated under the skin of armpit of each rat. The rats were divided into groups at random the next day and were administered with doses of NLEJ emulsion of 20 ml/kg, 10 ml/kg, 5 ml/kg iv × 10 (qd), and doses of cyclophosphamide of 30 ml/kg, 5 ml/kg iv × 10 (qd), the doses of cyclophosphamide were 30 mg/kg iv × 7 (qd), mg/kg iv × 2 (third and fifth). Tumor tissues from all treatments were sampled and weighed to calculate tumor inhibition ratios 14 days after inoculating.

Results

Anti-tumor therapeutical effect of NLEJ emulsion on ascites Walaer carcinosarcoma (solid) W256 was promoted by small dose chemotherapy of cyclophosphamide (Table 13).

TABLE 13

Anti-tumor Therapeutical Effect on Walaer Carcinosarcoma (Solid) W256 in vivo

| Sample | Dose (ml/kg) | Admin. | No. | Weight (g) | Inhibition (%) | P value |
|---|---|---|---|---|---|---|
| NLEJ | 20 | iv × 10 | 10/10 | 1.41 ± 0.78 | 58.16 | <0.01 |
| NLEJ | 10 | iv × 10 | 10/10 | 1/83 ± 0.77 | 45.69 | <0.01 |
| NLEJ | 5 | iv × 10 | 10/9 | 2.078 ± 1.1 | 38.34 | <0.01 |
| CTX | 10 mg | iv × 2 | 10/10 | 2.07 ± 1.11 | 38.58 | <0.01 |
| CTX | 30 mg | iv × 7 | 10/8 | 0.4 ± 0.15 | 88.13 | <0.01 |
| NLEJ + CTX | 20 ml + 10 mg | iv × 2 | 10/10 | 0.93 ± 0.34 | 72.40 | <0.01 |
| NLEJ + CTX | 10 ml + 10 mg | iv × 2 | 10/10 | 1.09 ± 0.5 | 67.66 | <0.01 |
| NLEJ + CTX | 5 ml + 10 mg | iv × 2 | 10/10 | 1.72 ± 0.91 | 48.96 | <0.01 |
| Blank | | iv × 10 | 10/10 | 3.37 ± 1.1 | — | — |

(2) Anti-tumor Therapeutical Effect on Sarcoma (S-180)

Methods

Sarcoma (S-180) tissues growing luxuriantly were prepared to be a cell suspension with physical saline 1:3(w/v). Mice were divided into groups at random the next day and were administered with doses of NLEJ emulsion of 25 ml/kg iv × 7 (qd), doses of cyclophosphamide of 30 mg/kg ip × 2 (second and fourth), doses of mitoxantrone (DHAD) of 2 mg/kg ip×2 (second and fourth), and doses of mitomycin of 1.5 mg/kg ip×2 (second and fourth). Tumor tissues from all treatments were sampled and weighed to calculate tumor inhibition ratios 14 days after inoculating.

Results

Results showed that anti-tumor therapeutic effect of NLEJ emulsion on sarcoma was enhanced by small doses of cyclophosphamide, DHAD and mitomycin (Table 14).

sampled from the angle of each mouse's eye, and leukocytes of the blood were counted.

Results

Table 15 and Table 16 show that NLEJ emulsion can protect mice from leukocyte decrease induced either from cyclophosphamide chemotherapy or from harringtonine chemotherapy.

TABLE 15

Protection of NLEJ Emulsion on Decrease of Leukocyte Induced by Cyclophosphamide Chemotherapy

| Medi. | Dose | Administration | No. 0 | Leucocyte number × 100/mm$^3$ (X + SD) 3 | 6 | 9 | 12 | 15 | 18 | 21 | 24 |
|---|---|---|---|---|---|---|---|---|---|---|---|
| CTX + NLEJ | 45 mg/kg + 12.5 ml/kg | ip × 1, 5, 9 + iv × 7 | 58 ±10 | 62 ±12 | 41 ±6 | 39 ±10 | 43 ±6 | 76** ±11 | 66** ±14 | 61* ±17 | 66** ±12 |
| CTX + NLEJ | 45 mg/kg + 6.25 ml/kg | ip × 1, 5, 9 + iv × 7 | 65 ±11 | 60 ±9 | 50 ±8 | 39 ±9 | 62 ±9 | 81** ±13 | 69** ±10 | 65** ±10 | 64* ±17 |
| CTX | 45 mg/kg | ip × 1, 5, 9 | 62 ±8 | 49Δ ±8 | 45Δ ±8 | 41Δ ±6 | 41Δ ±11 | 42Δ ±8 | 45Δ ±9 | 47Δ ±9 | 49Δ ±8 |
| Control | | | 58 ±7 | 69 ±2 | 69 ±2 | 68 ±2 | 88 ±3 | 82 ±2 | 81 ±4 | 86 ±2 | 72Δ ±2 |

Δ P < 0.001 compared with Control
** and * P < 0.01 and <0.05 compared with CTX

TABLE 16

Protection of NLEJ Emulsion on Decrease of Leukocyte Induced by Harringtonine Chemotherapy

| Medi. | Dose | Administration | Leucocyte number × 100/mm$^3$ (X + SD) 0 | 3 | 6 | 9 | 12 | 15 | 18 | 21 | 24 |
|---|---|---|---|---|---|---|---|---|---|---|---|
| HRTN + NLEJ | 1 mg/kg + 12.5 ml/kg | ip × 1, 5, 9 + iv × 7 | 59 ±8 | 73 ±10 | 61 ±6 | 56 ±11 | 81** ±5 | 89** ±9 | 75** ±16 | 79** ±20 | 97** ±20 |
| HRTN + NLEJ | 1 mg/kg + 6.25 ml/kg | ip × 1, 5, 9 + iv × 7 | 65 ±13 | 67 ±4 | 75 ±9 | 70 ±17 | 96** ±18 | 98** ±10 | 89** ±17 | 86** ±22 | 89** ±27 |
| HRTN | 1 mg/kg | ip × 1, 5, 9 | 60 ±9 | 75 ±5 | 65 ±10 | 50Δ ±10 | 44Δ ±10 | 43Δ ±7 | 49Δ ±8 | 53Δ ±9 | 56Δ ±9 |
| Control | 58 | 69 | 69 ±7 | 68 ±2 | 88 ±2 | 82 ±2 | 81 ±3 | 86 ±2 | 72Δ ±4 | ±2 | ±2 |

Δ P = 0.001 compared with Control
**P < 0.01 compared with HRTN

TABLE 14

Anti-tumor Therapeutical Effect on Sarcoma (S-180) in vivo

| Sample | Dose & Administration | No. | Inhibition (%) | P value |
|---|---|---|---|---|
| NLEJ | 25 ml/kg iv × 7 | 10/10 | 23 | <0.05 |
| NLEJ + CTX | 25 ml/kg + 30 mg/kg ip × 2 (1, 3) | 10/10 | 44 | <0.01 |
| CTX | 30 mg/kg ip × 2 (1, 3) | 10/10 | 39.4 | <0.05 |
| NLEJ ± DHAD | 25 ml/kg + 2 mg/kg ip × 2 (1, 3) | 10/10 | 67 | <0.01 |
| DHAD | 2 mg/kg ip × 2 (1, 3) | 10/10 | 50 | <0.01 |
| CLEG + mitomycin | 25 ml/kg + 1.5 m/kg ip × 2 (1, 3) | 10/10 | 67 | <0.01 |
| Mitomycin | 1.5 mg/kg ip × 2 (1, 3) | 10/10 | 39.4 | <0.05 |
| Control | 25 mg/kg ip × 2 (1, 3) | 30/10 | | |

Example 13

Protection of NLEJ Emulsion on Decrease of Leukocyte Induced by Chemotherapy

Methods

80 Swiss mice were divided into eight groups at random, were administered with cyclophosphamide at 45 mg/kg ip×3 (second, sixth and tenth), or harringtonine (HRTN) at 1 mg/kg ip×3 (second, sixth and tenth). To each of two of the medicine groups were administered NLEJ emulsion at the same time, at doses of 2.4 ml/kg and 6.25 ml/kg iv×7 (every day). At the beginning and on the fourth day of each administration, blood was Example 14

Clinical Therapeutic Effect of NLEJ Emulsion Methods

NLEJ Emulsion was administered intravenously or intraarterially in various human cancer therapies. Detail therapeutic methods is omitted.

Results

TABLE 17

Therapeutic Effect of NLW Emulsion

| Patient No. | CR | PR | NC | PD | Effective Ratio % |
|---|---|---|---|---|---|
| 51 | 0 | 26 | 19 | 6 | 50.98 |

TABLE 18

| Improvement of Symptom after Administration | | | | | | |
|---|---|---|---|---|---|---|
| Symptom | No. | Ease | Vanish | Unchange | Worse | Retarded % |
| Pain | 45 | 31 | 10 | 4 | 0 | 91.1 |
| Fever | 29 | 11 | 8 | 7 | 3 | 65.5 |
| Jaded appetite | 84 | 57 | 16 | 10 | 1 | 73.0 |
| Abdominal distension | 38 | 19 | 2 | 12 | 5 | 55.3 |
| Insomnia | 41 | 21 | 11 | 9 | 0 | 78.0 |
| Powerless | 70 | 37 | 16 | 9 | 8 | 75.7 |
| Cough | 28 | 14 | 6 | 8 | 0 | 71.4 |
| Breath with difficulty | 11 | 5 | 1 | 5 | 0 | 54.5 |
| Irregular Stool | 17 | 3 | 8 | 6 | 8 | 64.7 |

TABLE 19

| Enhancement of Human Immunity from NLEJ Emulsion | | | | | | |
|---|---|---|---|---|---|---|
| Immunity | Administ. | No. | Before | After | t value | P value |
| ANAE (%) | NLEJ | 40 | 39.38 ± 7.92 | 44.46 ± 13.41 | 2.477 | <0.05 |
|  | Chemotherapy | 19 | 50.05 ± 7.69 | 44.79 ± 6.64 | 2.580 | <0.05 |
| $OKT_1$ | NLEJ | 40 |  |  | 3.670 | <0.001 |
|  | Chemotherapy | 19 | 67.45 ± 4.60 | 62.91 ± 6.46 | 2.424 | <0.05 |
| $OKT_4/OKT_8$ | NLEJ | 40 | 1.09 ± 0.20 | 1.16 ± 0.33 | 2.098 | <0.05 |
|  | Chemotherapy | 19 | 1.39 ± 0.25 | 1.26 ± 0.28 | 2.424 | <0.05 |
| NK Cell (%) | NLEJ | 40 | 34.92 ± 12.41 | 43.91 ± 16.97 | 3.222 | <0.05<br><0.01 |

TABLE 20

| Protection of Marrow Function from NLEJ Emulsion | | | | | |
|---|---|---|---|---|---|
| Value | Therapy | No. | HB | WBC | PC |
| Increase | After | 102 | 80 | 85 | 79 |
| Unchange | After | 102 | 2 | 2 | 4 |
| Decrease | After | 102 | 20 | 15 | 19 |
| Effective % |  |  | 78.43 | 83.33 | 77.45 |
| Average | Before | 102 | 10.35 ± 1.77 | 4.82 ± 1.47 | 9.31 ± 4.27 |
|  | After | 102 | 10.64 ± 1.96 | 5.78 ± 1.70 | 10.70 ± 4.51 |
| t value |  |  | 2.343 | 6.302 | 5.070 |
| P value |  |  | <0.05 | <0.001 | <0.001 |

TABLE 21

| Improvement of Function of Liver and Spleen from NLEJ | | | | | | | |
|---|---|---|---|---|---|---|---|
|  |  | Before | | After | | | Retarded |
| Index | No. | Normal | Abnormal | Normal | Retarded | Unchange | (%) |
| Bilirubin | 70 | 52 | 18 | 52 ± 4 | 6 | 8 | 55.56 |
| G.P.T. | 70 | 58 | 12 | 58 ± 4 | 5 | 3 | 75.00 |

TABLE 22

| Strength Improvement from NLEJ Emulsion | | | | | | |
|---|---|---|---|---|---|---|
| KPS Evaluation | | | | | | |
| Patient No. | +30 | +20 | +10 | Stable | Decrease | Increasing % |
| 70 | 16 | 22 | 15 | 9 | 8 | 75.71 |

| | KPS Evaluation | | | | |
|---|---|---|---|---|---|
| Therapy | No. | >70 | 50–60 | <50 | $x^2$ | P value |
| Before | 70 | 15 | 28 | 27 |  |  |
| After | 70 | 39 | 18 | 13 | 21.159 | <0.001 |

| KPS Evaluation | NLEJ (n = 51) | Chemotherapy (n = 49) | $x^2$ | P value |
|---|---|---|---|---|

TABLE 22-continued

| Strength Improvement from NLEJ Emulsion | | | | |
|---|---|---|---|---|
| Before | >70 | 13 | 40 | |
|  | 50–60 | 18 | 7 | |
|  | <50 | 20 | 2 | 29.904 <0.001 |
| After | >70 | 31 | 20 | |
|  | 50–60 | 10 | 21 | |
|  | <50 | 10 | 8 | 6.459 <0.05 |
| $x^2$ |  | 12.934 | 17.266 | |
| P value |  | <0.001 | <0.001 | |

What is claimed is:

1. A neutral lipid isolated from the endosperm of Job's tears (NLEJ) consisting essentially of glycerides and alkylacylacetin, wherein the lipoclastic fatty acid residues of said NLEJ comprise saturated and unsaturated fatty acids, and wherein said neutral lipid has the following physicochemical properties: acid value <0.20, iodine value 95.00–107.00, saponification value 185.00–195.00, relative density 0.915–0.918 (20° C.) and diopter 1.470–1.475 (20° C.).

2. NLEJ of claim 1 wherein said glycerides comprise triglyceride, diglyceride and monoglyceride.

3. NLEJ of claim 1 wherein said glycerides comprises essentially the residues of hexadecanoic, octodecanoic, octadecenoic and octadecadienoic acid.

4. NLEJ of claim 2 wherein said neutral lipids is of following physicochemical indexes: acid value <0.20, iodine value 95.00–107.00, saponication value 185.00–195.00, relative density 0.915–0.918 (20° C.) and diopter 1.470–1.475 (20° C.).

5. NLEJ of claim 3 wherein said neutral lipids is of following physicochemical indexes: acid value <0.20, iodine value 95.00–107.00, saponication value 185.00–195.00, relative density 0.915–0.918 (20° C.) and diopter 1.470–1.475 (20° C.).

6. NLEJ of claim 1, isolated by a method comprising the steps of:
    (a) extraction with an organic solvent, absorption, and decoloration;
    (b) alkalizing saponification;
    (c) deemulsification by acetone; and
    (d) extraction by an organic solvent.

7. The NLEJ of claim 4, wherein said organic solvent of step (a) is acetone.

8. The NLEJ of claim 4, wherein said step (b) comprises the use of NaOH or KOH.

9. The NLEJ of claim 4, wherein said organic solvent of step (d) is petrol ether.

10. The NLEJ of claim 4, wherein said method further comprises, after one or more of said extraction of step (a), step (b), and step (d), the step of:

washing the emulsion with hot water.

11. A pharmaceutical composition with anti-tumor activity which comprises NLEJ of claim 1, emulsifier and distilled water.

12. The pharmaceutical composition of claim 11 wherein said composition is:

| NLEJ | effective amount |
| Emulsifier | q.s. |
| Isoosmoticum | q.s. |
| Distilled water | q.s. |

13. The pharmaceutical composition of claim 11 wherein said composition is:

| NLEJ | 5-25 g |
| Soy or egg lecithin | 0.3-3.0 g |
| Glycerol | 1.25-6 g |
| Distilled water | q.s. to 100 ml. |

14. The pharmaceutical composition of claim 11 wherein said composition is:

| NLEJ | 10 g |
| Soy lecthin for injection use | 1.5 g |
| Glycerol for injection use | 2.5 g |
| Water for injection use | q.s. to 100 ml. |

15. The pharmaceutical composition of claim 11 wherein said composition comprises other anti-tumor drugs.

* * * * *